(12) United States Patent
Bormet et al.

(10) Patent No.: US 12,582,303 B2
(45) Date of Patent: Mar. 24, 2026

(54) MEDICAL SCOPE WITH CAPACITIVE SENSOR UNIT

(71) Applicant: KARL STORZ Imaging, Inc., Goleta, CA (US)

(72) Inventors: Jonathan Bormet, Goleta, CA (US); Larry Oslie, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 522 days.

(21) Appl. No.: 18/060,225

(22) Filed: Nov. 30, 2022

(65) Prior Publication Data

US 2024/0172931 A1     May 30, 2024

(51) Int. Cl.
| | |
|---|---|
| *A61B 1/05* | (2006.01) |
| *A61B 1/00* | (2006.01) |
| *A61B 1/045* | (2006.01) |
| *A61B 1/06* | (2006.01) |

(52) U.S. Cl.
CPC ............ *A61B 1/05* (2013.01); *A61B 1/00045* (2013.01); *A61B 1/00059* (2013.01); *A61B 1/045* (2013.01); *A61B 1/0655* (2022.02)

(58) Field of Classification Search
CPC .............. A61B 1/00039; A61B 1/0004; A61B 1/00042; A61B 1/00059; A61B 1/00062; A61B 1/00066; A61B 2017/00207; A61B 2017/00398; A61B 2017/00424; A61B 2090/062; A61B 2562/0214; A61B 2562/0257; A61B 2034/358; G06F 3/017; G06F 3/03547; G06V 40/12; H03K 17/962; H03K 17/9622
See application file for complete search history.

(56) References Cited

U.S. PATENT DOCUMENTS

| | | | | |
|---|---|---|---|---|
| 2012/0157776 A1* | 6/2012 | Wood | ................... | A61B 3/0008 |
| | | | | 315/227 R |
| 2013/0201309 A1* | 8/2013 | Takahashi | .......... | A61B 1/00042 |
| | | | | 348/65 |
| 2015/0099925 A1 | 4/2015 | Davidson et al. | | |
| 2017/0119474 A1* | 5/2017 | Kronman | ............. | A61B 90/361 |
| 2019/0000302 A1* | 1/2019 | Doser | ................ | A61B 1/00066 |
| 2019/0133430 A1* | 5/2019 | Inglis | ................... | A61B 1/0005 |

(Continued)

FOREIGN PATENT DOCUMENTS

| | | |
|---|---|---|
| WO | 2021048840 A1 | 3/2021 |

OTHER PUBLICATIONS

Lee, Kang Ha, International Search Report and Opinion, Mar. 29, 2024, pp. 1-10, WIPO, South Korea.

*Primary Examiner* — Michael J Carey
*Assistant Examiner* — Stephen Floyd London
(74) *Attorney, Agent, or Firm* — David N. Villalpando; Jacqueline Cohen

(57)     ABSTRACT

Provided is an imaging system including a video endoscope, the video endoscope having a handle, and an endoscope. The endoscope includes an image sensor fixedly mounted within the endoscope. A capacitive sensing unit is disposed along an outer surface of the handle. The capacitive sensing unit includes a plurality of capacitive sensors disposed on the outer surface of the handle. The handle includes an electronic controller operable to process an actuation of the plurality of capacitive sensors so as to control a camera control function and determine a medical procedure and/or an identity of the user.

14 Claims, 7 Drawing Sheets

(56)      References Cited

U.S. PATENT DOCUMENTS

| | | |
|---|---|---|
| 2019/0159656 A1* | 5/2019 | Hale .................. A61B 1/00045 |
| 2019/0261844 A1* | 8/2019 | Walker .................. A61B 1/267 |
| 2019/0290102 A1* | 9/2019 | Sasaki ................ A61B 1/00042 |
| 2019/0357871 A1* | 11/2019 | Conwell ................ A61B 6/566 |
| 2020/0009341 A1* | 1/2020 | Blom ................ A61M 16/0472 |
| 2021/0100431 A1* | 4/2021 | Shainwald ......... A61B 1/00066 |
| 2021/0321864 A1* | 10/2021 | Bloembergen ....... A61B 5/0071 |
| 2022/0022988 A1 | 1/2022 | Savall et al. |
| 2022/0409024 A1* | 12/2022 | Kambe ............. A61B 1/00128 |
| 2024/0148242 A1* | 5/2024 | Schack ............... A61C 9/0053 |

* cited by examiner

Method of Operating an Imaging System  ——  500

MEDICAL SCOPE WITH CAPACITIVE SENSOR UNIT

TECHNICAL FIELD

The disclosure relates generally to the field of medical imaging scopes and more specifically to endoscope designs for improving user control of medical scopes.

BACKGROUND

A typical prior art optical endoscopic system 1, as illustrated in FIG. 1A, usually includes a first imaging lens (e.g., an objective) or lenses followed by a series of carrier lenses (e.g., relays), collectively an optical assembly 3 in the endoscope 4, which captures and transmits an optical image from inside of an enclosed area 5, such as internal to a human or animal body, to the outside of the enclosed area, where the image light can be captured and/or analyzed. The proximal end of the endoscope 2 may be attached, via direct coupling or an adaptor, to a camera head 6 or an eye-piece for viewing. The camera head 6 usually includes lenses for receiving the optical image and forming a real optical image onto an image sensor contained therein. The digital image captured by the image sensor can then be transmitted to a camera control unit or other similar modules for analysis, processing, and display. A variation on the described optical endoscope, often referred to as a video endoscope, is illustrated in FIG. 1B. In a video endoscope 12, the endoscopic shaft 14 is electronically connected to a handle 16. An optical system including an imaging lens (e.g., an objective) or lenses 18 is followed by an image sensor 20, which is usually placed at the distal end 22 of the endoscopic shaft 14 to receive the optical image formed by the imaging lens or lenses 18. The image sensor 22 converts the image data into an electronic signal which is transmitted down the length of the shaft 14 by electronic transmission means 24, such as wire, cable, a flexible circuit board, etc., to the handle 16, which may contain image processing circuitry, and or may be connected to a camera control unit for further processing, analysis, and/or display. The camera head 6, in the case of an optical endoscopic system 2, or the handle 16, in the case of a video endoscope 12 will typically comprise one or more buttons 7, 17 positioned on an outer surface of the camera head 6, usually the top surface, but buttons 7, 17 may be positioned on multiple surfaces. The buttons 7 are depressible and may present very small slits or grooves on the outer surface of the camera head 6 or handle 16, which can be difficult to clean and sterilize.

Often, in the course of an endoscopic procedure, the user will want to rotate the endoscopic shaft relative to the body under observation. This is particularly advantageous when the endoscopic shaft has a viewing angle that is not parallel to the longitudinal axis of the shaft. For example, endoscopes with a 30° viewing angle relative to the longitudinal axis are common (such as that shown at the distal end of the shaft of the endoscopes shown in FIGS. 1A and 1B), and by rotating the shaft of such a scope, the field of view may be changed, permitting the surgeon to visualize different areas of the scene, as opposed to a 0° viewing angle endoscope, which will have the same field of view, regardless of rotation. In a conventional optical endoscope, such as that shown in FIG. 1A, the field of view may be changed by rotating the endoscopic shaft 4 relative to the camera head 6. As the image light is relayed optically from the distal end to the image sensor contained within the camera head 6, the rotational orientation (i.e., "horizon") remains constant, regardless of the rotational position of the shaft 4. Therefore, it is common practice for a surgeon to grasp the light post 8, located near the proximal end of the shaft 4, in order to drive the shaft rotation relative to the camera head 6, the proximal end of the endoscope 4 generally ending in an eyecup which is connected by a bayonet connection, and thus permits the entire endoscope to rotate freely with respect to the camera head. By contrast, in a video endoscope, such as that shown in FIG. 1B, the shaft 4 containing the image sensor 20 is rigidly connected to the handle, therefore it is not possible to rotate either the handle with respect to the shaft, nor the shaft with respect to the handle. Therefore, if a change in the field of view is desired, the handle may be rotated, but this carries with it the often deleterious effect of also rotating the image sensor itself, resulting in the displayed image also being rotated Some conventional video endoscopes utilize orientation-determining devices, such as gyroscopes or inertial measurement unit (IMU), to detect a rotation of the endoscopic device, and to, by means of image processing, adjust the image such that it retains a constant or otherwise desired horizon.

What is needed are systems and methods to enable the maintenance of a constant image horizon independent of the rotation of video endoscope without the use of orientation-determining devices, as well as systems to allow flexibility of the user to determine and set a desired image horizon. What is also needed is an endoscope without buttons to provide a smooth surface that can be easily mechanically cleaned relative to endoscopes with buttons. Further, a greater versatility of control of various camera and endoscopic functions without the need for complicated mechanical and/or manual controls is desired.

SUMMARY

A medical scope is provided that is configured to facilitate user operation and sanitation procedures. In another aspect of the disclosure, the medical scope is further configured to process a touch to control a camera function, detect the identity of the user and detect a medical use of the scope.

In a first aspect of the disclosure, the medical scope is a video endoscope. The video endoscope includes an endoscope having an image sensor fixedly mounted within the endoscope. The video endoscope further includes a handle rigidly attached to the endoscopic shaft and a capacitive sensing unit disposed along an outer surface of the handle. The capacitive sensing unit includes a plurality of capacitive sensors arranged radially along a surface of the handle. The handle further includes an electronic controller configured to process an actuation of the plurality of capacitive sensors so as to control a camera control function, such as a rotation of the image.

In some implementations of the video endoscope, the plurality of capacitive sensors forms a ring. In other implementations of the video endoscope, the plurality of capacitive sensors are disposed at a distal end of the handle. In yet another implementation of the video endoscope, an outer surface of the handle is smooth and uninterrupted.

In yet another implementation of the video endoscope, a predetermined number of capacitive sensors of the capacitive sensing unit is disposed on an outer surface of the endoscope. In such an implementation, an outer surface of the endoscope and the outer surface of the handle form a contiguous and continuous surface. The electronic controller may be further configured to process a grip detected by the capacitive sensing unit to determine a likely medical procedure and configure the system accordingly. Examples of system configuration include image processing parameters such as auto-exposure settings and color preferences. In such an aspect, the capacitive sensing unit is further configured to detect a fingerprint and/or the grip and the electronic controller processes the fingerprint and/or the grip so as to determine an identification of the user. User identification may then be used to load system configuration presets.

In yet another aspect, the predetermined number of capacitive sensors of the capacitive sensing unit disposed on an outer surface of the endoscopic shaft extends along a length of the endoscope. In such an aspect, the electronic controller is further configured to process a signal detected by the predetermined number of capacitive sensors of the capacitive sensing unit disposed on an outer surface of the endoscope when the endoscope is inserted into a patient to determine a depth the endoscopic shaft is inserted.

A method of operating a video endoscope is also provided herein. The method includes the steps of providing a video endoscope. The video endoscope includes an endoscope having an image sensor fixedly mounted within the endoscope, a handle attached to the endoscopic shaft, and a capacitive sensing unit disposed along an outer surface of the handle. The handle includes an electronic controller, and the capacitive sensing unit includes a plurality of capacitive sensors.

The method includes the step of touching the capacitive sensing unit so as to actuate the plurality of capacitive sensors. The method includes the step of processing, by the electronic controller, the actuation of the plurality of capacitive sensors so as to control a camera function. The touching may be sliding a finger along the capacitive sensing unit, and the camera control function is a rotation of an image in accordance with a direction of the slide. In other aspects, the camera control function is turning off or adjusting the intensity of an illumination source.

In some implementations, the method further includes the step of arranging the plurality of capacitive sensors so as to form a ring.

In some aspects, a predetermined number of capacitive sensors of the capacitive sensing unit is further disposed on an outer surface of the endoscope. In such an aspect, the method may further include the step of determining by the electronic controller a medical procedure by processing a grip detected by the capacitive sensing unit to determine the medical procedure. The method may further include the step of displaying the medical procedure on a display. In such an aspect, the method may further include the step of confirming the medical procedure by actuating an input communicatively coupled to the camera control module.

In some implementations of the method, the method may further include the step of determining by the electronic controller an identification of a user by processing a fingerprint and/or a grip detected by the capacitive sensing unit to determine the identity of the user and may display the identification of the user on a display. In such an implementation, the method may further include the step of confirming the identification by actuating an input communicatively coupled to the camera control module, wherein the input is further configured to enter a user identification. In yet another aspect of said implementation, the method may further include the step of configuring a parameter of the video endoscope to a user preference, the user preference associated with the identification determined by the electronic controller.

In yet another aspect of the method, the predetermined number of capacitive sensors of the capacitive sensing unit is disposed on an outer surface of the endoscope and extends along a length of the endoscope. In such an aspect, the method further includes the step of calculating by the electronic controller, a depth of the endoscope inserted into a patient, the electronic controller processing a signal detected by the predetermined number of capacitive sensors of the capacitive sensing unit disposed on an outer surface of the endoscope when the endoscope is inserted into a patient so as to calculate the depth in which the endoscope is inserted.

BRIEF DESCRIPTION OF THE DRAWINGS

The present disclosure will become more fully understood from the detailed description given herein and the accompanying drawings, which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras and Fluorescence Image sensors (referenced herein as "FI sensors") and related circuitry for signal capture and processing are well-known, the present description will be directed in particular to elements forming part of, or cooperating more directly with, a method and apparatus in accordance with the disclosure. Elements not specifically shown or described herein are selected from those known in the art. Certain aspects of the embodiments to be described are provided in software. Given the system as shown and described according to the disclosure in the following materials, software not specifically shown, described, or suggested herein that is useful for implementation of the disclosure is conventional and within the ordinary skill in such arts.

An imaging system includes a video endoscope, including a handle and an endoscopic shaft attached to the handle. The endoscopic shaft includes an image sensor fixedly mounted within the shaft. The video endoscope further includes a capacitive sensing unit disposed along an outer surface of the handle. The capacitive sensing unit includes a plurality of capacitive sensors, which may be arranged radially along the surface of the handle. The handle includes an electronic controller operable to process an actuation of the plurality of capacitive sensors so as to control a camera control or image processing function, such as controlling the rotation the image displayed, adjusting the intensity of an illumination source, or adjusting focus, optical or digital zoom, or image contrast. As used herein, a camera control function refers to any of these controls or manipulations of the image generated or captured by the video endoscope or a system to which it is connected, such as a camera control unit (CCU) or illumination source. In other aspects, the actuation of the capacitive sensing unit is processed to determine an identification of the user, a medical procedure, or a depth in which the endoscope is inserted into a patient. In other aspects, the video endoscope has a smooth and continuous surface to facilitate cleaning the video endoscope.

Figure 1A:
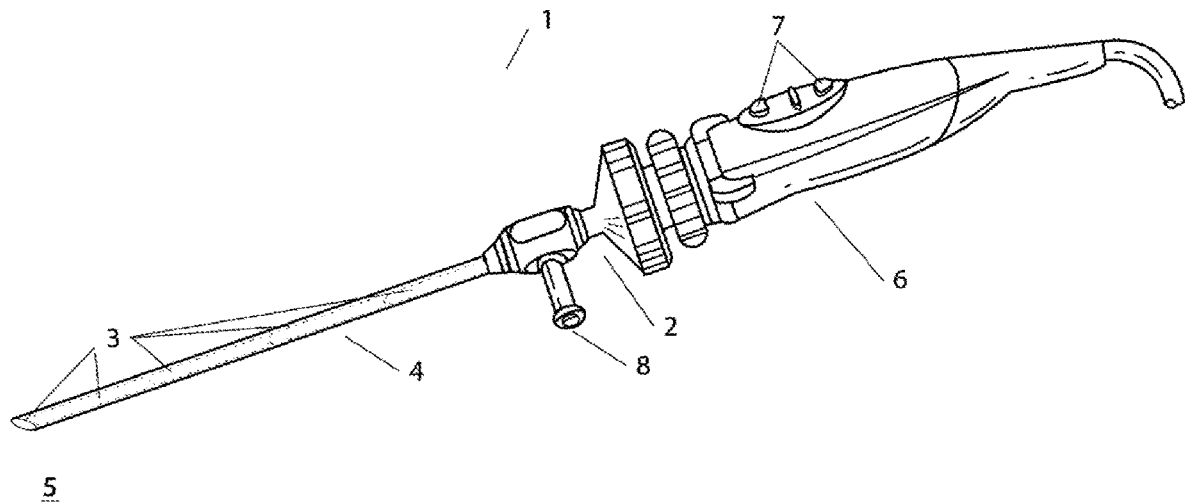
FIG. 1A is a diagram of a prior art optical endoscopic system including a conventional optical relay endoscope and a camera head containing an image sensor.
Figure 1B:
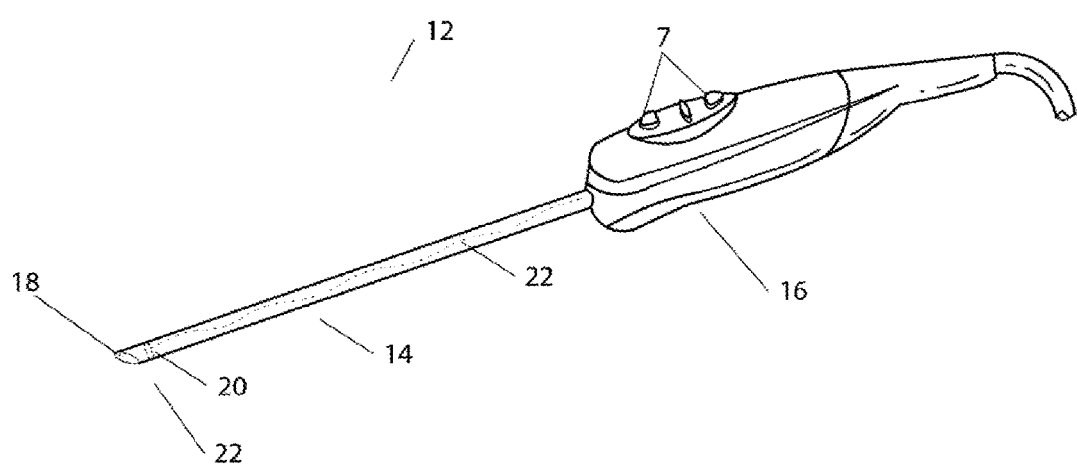
FIG. 1B is a diagram of a prior art video endoscope including an endoscopic shaft and a handle.
Figure 2:
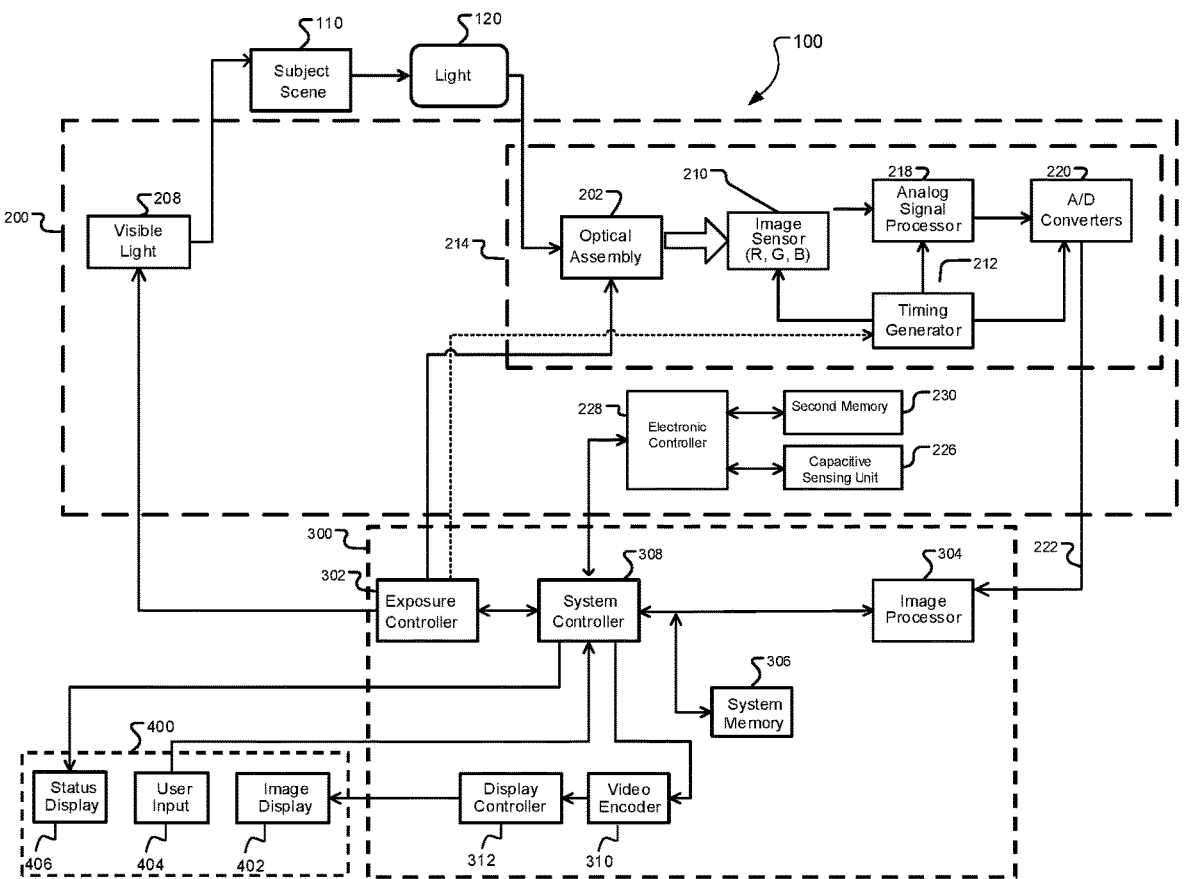
FIG. 2 is a hardware block diagram of an example system, including a video endoscope, a camera control module, and a user interface.

Referring to FIG. 2, shown is a system hardware block diagram of an example imaging system 100, including a video endoscope 200, a camera control module 300, and a user interface 400, including one or more displays, the system 100 being one example hardware design on which the camera control functions described herein may be implemented. The exemplar video endoscope 200 in this system 100 is a standard visible light imaging video endoscope. However, this is not limiting, and features and techniques herein may be employed with many types of scopes-including visible light/fluorescence imaging scopes. Of the depicted blocks, video endoscope 200 includes an optical assembly 202, a handle 204, and an endoscopic shaft 206 (see FIGS. 3-8). The endoscopic shaft 206 is fixed to the handle 204. The endoscopic shaft 206 includes an image sensor 210 fixedly mounted within the shaft. The video endoscope 200 also includes a light source 208 for illuminating a subject scene. The disclosure may be applicable to more than one type of device enabled for image capture, such as endoscopes, digital microscopes and, other medical imaging devices for example.

The light source 208 may be configured to illuminate a subject scene 110. Light source 208 may include a single light-emitting element configured to provide light throughout the desired spectrum, one or more visible light-emitting elements, and/or one or more fluorescent excitation light-emitting elements. Further, light source 208 may include fiber optics passing through the body of the scope 200, or other light emitting arrangements, such as LEDs or laser diodes distally positioned at or near the front of the scope 200. As shown in the drawing, light 120 reflected, scattered, and/or emitted, from the subject scene 110 is passed to the optical assembly 202 and is focused toward an image sensor 210. In the circumstance wherein the video endoscope is a visible light-FI scope more button functions may be desired to change between visible and FI mode and thus can benefit greatly from the techniques described herein.

As shown in FIG. 2, optical assembly 202 includes at least one lens (not shown), which may be a wide-angle lens element such that optical assembly 202 focuses light representing a wide field of view. In some embodiments of the invention, the handle 204 contains control electronics, and the image sensor 210 is located in the endoscopic shaft 206 itself, often toward the distal end of the endoscopic shaft 206. The optical assembly 202 may be contained together in a single imaging device with the image sensor 210. The solid-state image sensor 210 may be an active pixel complementary metal oxide semiconductor sensor (CMOS APS), a charge-coupled device (CCD), or other suitable image sensor (or sensors) known in the art to convert light into electrical signals.

Timing generator 212 produces various clocking signals to select rows and pixels and is configured to synchronize the operation of image sensor 210. Image sensor unit 214 typically includes the solid-state image sensor 210, adjustment control 216, the analog signal processor 218, the A/D converter 220, and the timing generator 212. The individual components of the image sensor unit 214 can be fabricated as a single integrated circuit, as is commonly done with CMOS image sensors, or they can be separately-fabricated integrated circuits.

The total amount of light 120 reaching the image sensor(s) 210 is regulated by the intensity of the light source 208, the size of an aperture of the optical assembly 202, and the time for which the image sensor(s) 210 integrates charge. The amount of light provided to the image sensor(s) 210 may be controlled by the camera control unit 300. For example, the camera control unit 300 includes an exposure controller 302, which responds to the amount of light available in the scene given the intensity and spatial distribution of digitized signals corresponding to the intensity, and spatial distribution of the light focused on the image sensor 210. Exposure controller 302 may also control the aperture of the optical assembly 202 and, indirectly, the time for which the image sensor(s) 210 integrate charge. The control connection from exposure controller 302 to the timing generator 212 is shown as a dotted line because the control is typically indirect.

Analog signals from the image sensor(s) 210 are processed by analog signal processor 218 and applied to the A/D converter 220 for digitizing the analog signals from the image sensor(s) 210. The digitized signals, each representing streams of images or image representations based on the data, are transmitted to the image processor 304 as image signal(s) 210.

The image processor 304 is disposed in the camera control unit 300 and is configured to perform digital image processing to process and filter, as appropriate, the received images. The image processor 304 may execute algorithms stored in a system memory 306 for processing the collected images. It should be noted that in some embodiments, the CCU, or some elements thereof, may be contained with the handle.

The camera control unit 300 further includes a system controller 308 that controls the overall operation of the video endoscope 200 based on a software program stored in system memory 306. The system memory 306 can also be used to store user setting selections and other data that is saved when the video endoscope 200 is turned off.

The system controller 308 controls the sequence of data captured by directing the exposure controller 302 to set the light source 208 intensity and the size of the aperture of the optical assembly 202 and control various filters in optical assembly 202.

Processed image data is continuously sent to the video encoder 310 to produce a video signal which is processed by display controller 312 and presented on image display 402. Image display 402 may be a liquid crystal display backlit with light-emitting diodes (LED LCD), although other displays can be used as well. The processed image data may be stored in system memory 306 or other internal or external memory devices, such as SD cards, USB drives, external hard drives, or cloud-based storage solutions.

The user interface 400, including all or any combination of image display 402, user inputs 404, and status display 406, is controlled by a combination of software programs executed by the system controller 308, receiving input from user inputs 404. User inputs 168 typically include some combination of typing keyboards, computer pointing devices, touch screens, voice command processing devices, or similar user input devices. The system controller 308 manages the graphical user interface (GUI) presented on one or more displays (e.g., image display 402).

In addition to the system controller 308 and exposure controller 302, electronic circuitry may include programmable logic devices, processors, or controllers. The image processor 304, system memory 306, video encoder 310, and display controller 312 may be housed within the camera control unit (CCU) 300.

CCU 300 may be responsible for powering and controlling light source 208, the image sensor 210, and/or optical assembly 202, and may receive power and signals directly from the video endoscope 200 or indirectly by actuation of a user input 404 on the image display 402, such as an icon on a touch screen or by manipulation of a GUI by a mouse. Such power and control connections are not depicted separately but will typically be contained in a single flexible cable with data connections.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits.

Although a combination of such programmable logic devices, processors, or controllers has been described, it should be apparent that one programmable logic device, digital signal processor, microcontroller, or other digital logic circuits can be designated to perform all of the needed functions. All of these variations can perform the same function and fall within the scope of this invention.

Figure 3:
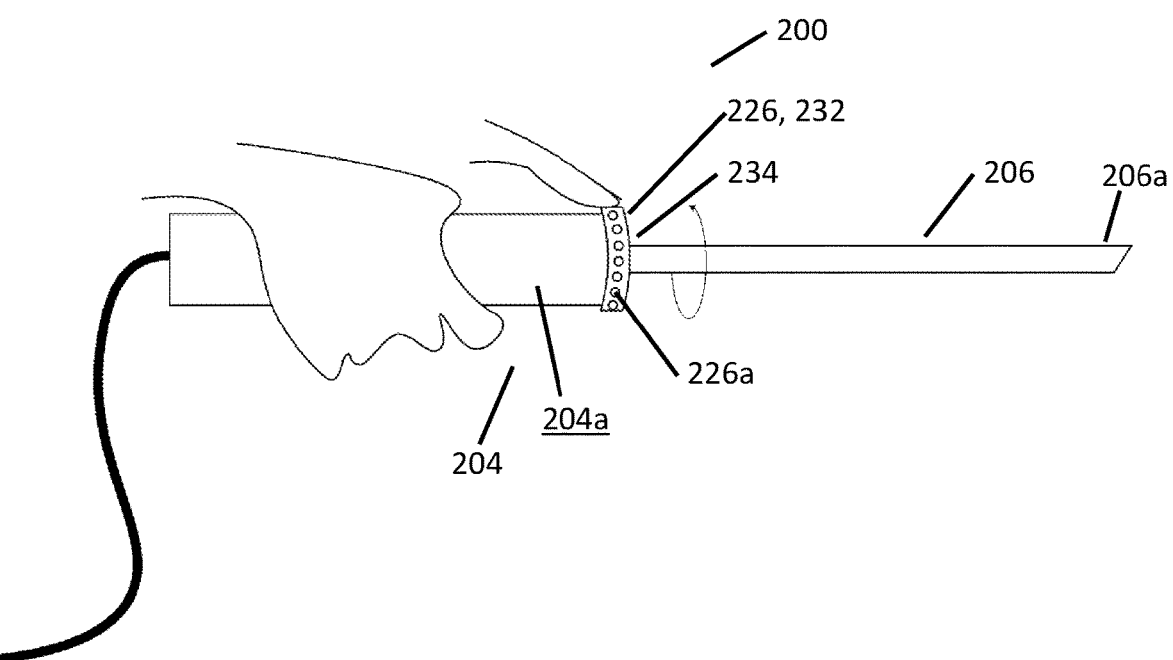
FIG. 3 is an illustrative depiction of a video endoscope in accordance with the principles of a first embodiment described herein.

With reference now to FIG. 3, an illustrative depiction of the video endoscope 200 is provided. As stated above, the video endoscope 200 includes a handle 204 and an endoscopic shaft 206. The handle 204 includes an outer surface 204a and is dimensioned to be gripped by a user. Though the depiction of the handle 204 is shown as being cylindrical, it should be appreciated that the handle 28 may include contours and dimensions for facilitating a grip.

A capacitive sensing unit 226 is disposed on the outer surface 204a of the handle 204. The capacitive sensing unit 226 includes a plurality of capacitive sensors 226a. It should be appreciated that the term "outer surface" need not require that the capacitive sensors 226a are exposed to the environment but should be construed to mean that capacitive sensing unit 226 and the plurality of capacitive sensors 226a are positioned adjacent to the outer surface to be able to receive tactile responses from a grip of the user. Thus, protective films and layers may cover the capacitive sensing unit 226, and the capacitive sensing unit 226 may still be construed to be disposed on the outer surface of the handle 28. The capacitive sensing unit 226 should not require significant pressure to activate but requires sufficient contact to disrupt a dielectric field. Thus, a touch is sufficient to actuate the plurality of capacitive sensors 226a (i.e., disrupting the dielectric field in a manner that transmits a signal). The capacitive sensing unit 226 may be in the form of a film or a sheet of dielectric material, and any capacitive sensing unit 226 currently known or later developed may be incorporated herein. The outer surface 204a of the handle 204 may be smooth and continuous, meaning that there are no irregularities that may trap debris, biologic material, or the like, thus facilitating the mechanical cleaning and chemical sterilization of the video endoscope 200.

The handle 204 further includes an electronic controller 228 communicatively coupled to the capacitive sensing unit 226. The electronic controller 228 is configured to process an actuation of any of the plurality of capacitive sensors 226a so as to control a camera control function, such as a rotation, zoom, lighting, and the like. The handle 204 further includes a second memory 230. The second memory 230 is a non-volatile, non-transitory memory configured to store an algorithm executable by the electronic controller 228 to process signals from the capacitive sensing unit 226 to determine the camera function to be controlled and instructions for controlling the camera function. In one aspect, the electronic controller 228 is operable to process signals from the capacitive sensing unit 226 to control the camera function. As described above, the signals may be generated in response to the disruption of a dielectric field by a touch. Alternatively, the electronic controller 228 may be configured to process signals from the capacitive sensing unit 226 to send instructions to the camera control unit 300, wherein the system controller 308 processes the instructions to perform and control the determined camera function. In other aspects, the electronic controller 228 may be configured to process the signals from the capacitive sensing unit 226 to determine an identification of a user or determine the medical procedure. In such an aspect, the identification of the user and/or the determined medical procedure is transmitted to the system controller 308, wherein the system controller 308 may be configured to process the user identification and the determined medical procedure to set the video endoscope 200 to a corresponding operating parameter, as discussed in greater detail below.

In some embodiments a plurality of capacitive sensors 226a may be arranged annularly along the outer surface 204a of the handle 204, forming a "control ring." While embodiments employing such a control ring may be useful for many applications, one exemplar application involves maintaining a desired image horizon while rotating the video endoscope. This control in some ways mimics the rotation control used by many surgeons in rotating an endoscope to achieve a new field of view by grasping the light post of a conventional optical endoscope, as discussed above. In these embodiments a user may touch the control ring, activating capacitive sensors 226a contained thereon. As the camera control unit 300 is communicatively coupled to the video endoscope 200 and is further operable process image data gathered by the image sensor 210 to generate an image or video as described above, the activation of this horizon control ring can set the default image horizon to that being displayed at the time the horizon ring control is activated. The user can then rotate the handle 204, and thereby the endoscopic shaft 206 to change the direction of view, as discussed before, however, while the horizon control ring is activated, i.e., touched, and rotated beneath the activating digit of the user, the CCU can process the incoming image data counter-rotate the collected image, such that the displayed image retains the horizon selected when the horizon control ring is initially touched. When the horizon control ring is de-activated (by removal of the activating digit), the present displayed horizon can be retained as the new default horizon. Alternatively, of course, the horizon can be adjusted by moving an activating digit along the horizon control ring without rotating the handle, for example, if the current horizon is set incorrectly. While such a "capacitive control ring" is particularly advantageous for display horizon control, it should be appreciated that such a control ring (or a plurality thereof) have several other useful applications, as they may mimic the controls that have become familiar to surgeons. Therefore, capacitive control rings may also be used to adjust zoom or focus, for example.

As shown in the aspect of FIG. 3, and discussed above, the capacitive sensors 226a form a ring 232. The ring 232 is shown disposed at a distal end 204b of the handle 204 so as to be adjacent to the endoscopic shaft 206. The ring 232 may be continuous so as to be arranged around the entire circumference of the handle 204 or may be semi-circular so as to have two ends.

In some aspects the electronic controller 228 is configured to, for example, rotate the displayed image in a manner that is not commensurate with the slide of a finger along a control ring. For instance, five degrees of sliding a finger along the ring 232 may result in one (1) degree of rotation in the image. It should be appreciated that the image is shown on the image display 402 and that the rotation of the image on the display 402 is contemporaneous with the sliding of the finger.

Figure 4:
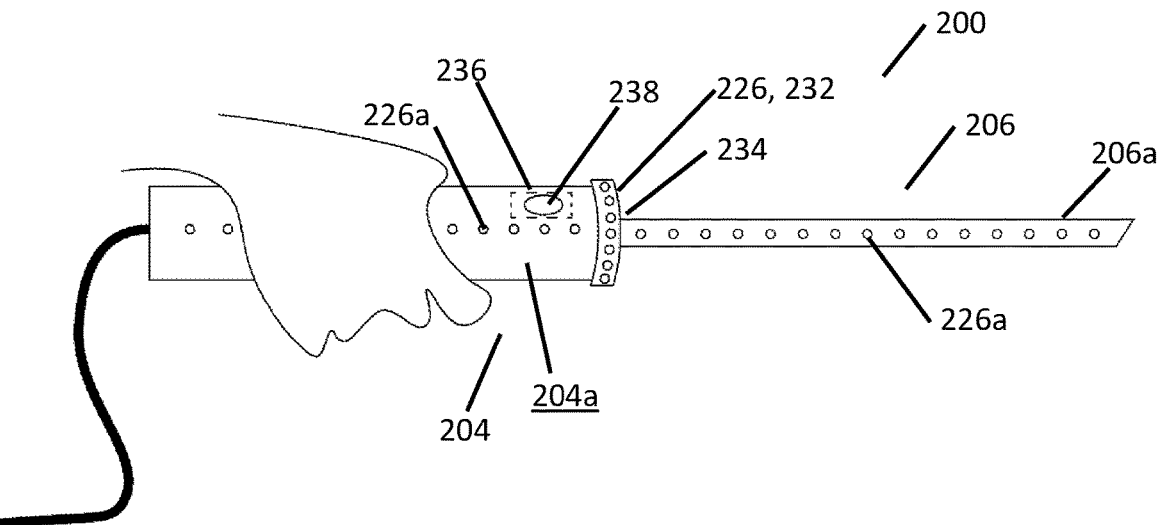
FIG. 4 is an illustrative depiction of a video endoscope in accordance with the principles of a second embodiment described herein, wherein the handle is gripped.

With reference now to FIG. 4, another aspect of the imaging system 100 is provided wherein a predetermined number of capacitive sensors 226a of the capacitive sensing unit 226 is disposed on an outer surface 206a of the endoscopic shaft 206. Preferably, the endoscopic shaft 206 is fixedly attached to the handle 204 so as to form a single and unitary device. In such an aspect, the outer surface 206a of the endoscopic shaft 206 and the outer surface 204a of the handle 204 form a contiguous and continuous surface, meaning there are no irregularities that may trap debris, biologic material, or the like. Accordingly, there is no transition in the outer surface 206a of the endoscopic shaft 206 and the outer surface 204a of the handle 204. In one aspect, the area 234, where the endoscopic shaft 206 and the handle 204 is joined, is rounded so as to provide easy access to said area 120 to facilitate the cleaning of said area 234.

The capacitive sensing unit 226 may be further disposed along the outer surface 204a of the handle 204 so as to facilitate the detection of a grip or a fingerprint. In such a configuration, the electronic controller 228 processes the grip to determine a medical procedure and/or an identification of the user. With reference again to FIG. 4 and now to FIG. 5, an operation of the video endoscope 200 configured to determine a medical procedure is provided. FIG. 4 shows an instance where the user grips the handle 204 of the video endoscope 200. As such, signals from the capacitive sensors 226a, which are contacted by the grip are processed by the electronic controller 228 to determine that the video endoscope 200 is being held by the handle 204 alone. That is, no signals corresponding to a grip are transmitted by the capacitive sensors 226a disposed on the outer surface 206a of the endoscopic shaft 206 as the endoscopic shaft 206 is not gripped. The capacitive sensing unit 226 is shown disposed along an entire length of the handle 204 and an entire length of the endoscopic shaft 206. It should be appreciated that though the capacitive sensors 226a are illustratively shown as being arranged along an axis of the handle 204, the capacitive sensors 226a may be disposed to cover other areas of the outer surface 204a of the handle 204, and the number and arrangement of the capacitive sensors 226a is not limiting to the scope of the appended claims. One skilled in the art would appreciate that the number and location of the capacitive sensors 226a of the capacitive sensing unit 226 is selected to determine a grip, and thus configurations of the capacitive sensing unit 226 other than what is shown fall within the scope of the appended claims. FIG. 4 shows the handle 204 being gripped, wherein the electronic controller 228 processes the signal from the capacitive sensing unit 226 to determine a likely medical procedure that is associated with the handle 204 being so gripped; such a determination may be made with respect to the location of the grip and the profile of the grip.

Figure 5:
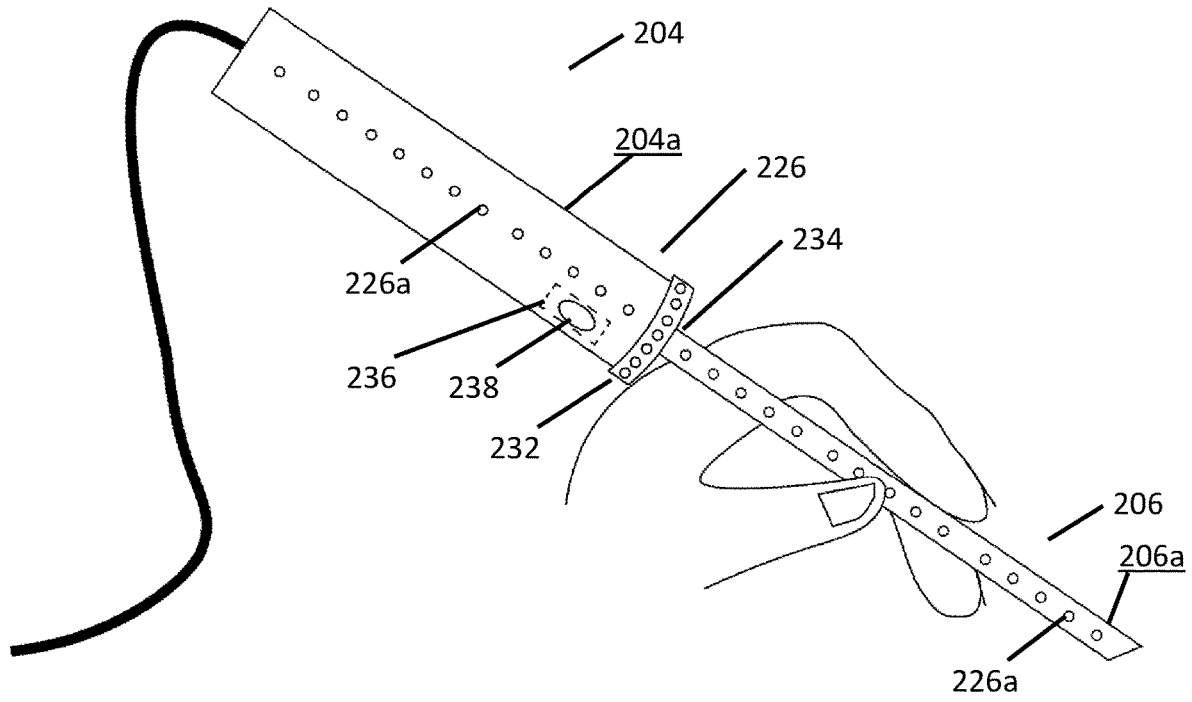
FIG. 5 is an illustrative depiction of the video endoscope shown in FIG. 4, wherein the endoscopic shaft is gripped.

FIG. 5 depicts an instance where the video endoscope 200 is being held by the endoscopic shaft 206 alone. In such an aspect, the electronic controller 228 processes the signal from the capacitive sensing unit 226 to determine a medical procedure associated with the endoscopic shaft 206 being so gripped. In instances where a portion of the endoscopic shaft 206 and the handle 204 are gripped simultaneously, the electronic controller processes the signal from the capacitive sensing unit 226 to determine a medical procedure associated with the endoscopic shaft 206 and the handle 204 being so gripped simultaneously. It should be appreciated that the electronic controller 228 may be configured to determine a grip by processing a predetermined response from the capacitive sensing unit 226, wherein a signal from a single capacitive sensor 226a on the outer surface 206a of the endoscopic shaft 206 or the outer surface 204a of the handle 204 may be determined as the handle 204 or the endoscopic shaft 206 as not being gripped, as the case may be. Thus, should the handle 204 be gripped and a finger incidentally touches the endoscopic shaft 206, resulting in a signal from a capacitive sensor 226a on the endoscopic shaft 206, said signal may be disregarded or may be processed to determine that said signal is not a grip. The electronic controller 228 may be configured to take into consideration other factors to determine a grip, such as the number of signals received from adjacent capacitive sensors 226a, or a duration of a signal transmitted from the capacitive sensor 226a. It should be appreciated that the aspect wherein a grip is processed to determine a medical process may be used in conjunction or may stand alone with the aspect where an actuation of the capacitive sensing unit 226 is processed to rotate the image, as described in FIG. 3.

In aspects where a grip is processed to determine a medical procedure, the second memory 230 may include a list of medical procedures, each having a grip profile associated with a medical procedure. As used herein, the term "grip profile" is construed as a shape of a grouping of actuated capacitive sensors 226a. Each medical procedure may further include a set of camera operating parameters, wherein the electronic controller 228 or the system controller 308 are further configured to set the video scope 200 to the corresponding camera operating parameters. The operating parameters may include illumination distribution, light intensity, depth of field settings, HDR settings, etc. For example, a video endoscope 200 gripped by the endoscopic shaft 206 may be indicative of operation in an ENT (ear, nose, and throat) procedure. Such procedures may include the insertion of the distal tip of the endoscope through a lumen, such as an ear canal. Under such circumstances, it may be beneficial to, for example, activate forward facing distally placed LED illumination sources, and deactivate illumination sources that are positioned to illuminate peripherally to the endoscopic tip, providing thereby, more illumination down the lumen and less illumination at the periphery, which would overwhelm the image sensor, and cause the central region to appear too dark. The grip may be processed to automatically control the camera operating parameters. For instance, in cases where the light source 208 is actuated, the video scope 200 may be configured to automatically turn off the light source 208 and enter a sleep state when no grip is detected for a period of time, such as when the video scope 200 is laid down.

With reference again to FIGS. 4 and 5, in another aspect of the imaging system 100, the capacitive sensing unit 226 is further configured to detect a unique identifying biometric marker, such as a fingerprint and/or a grip profile, and the electronic controller 228 processes the unique identifying biometric marker so as to determine an identification of the user. In such an aspect, the electronic controller 228 processes the signals from the capacitive sensing unit 226 to determine a fingerprint and/or a grip. In such an aspect, the capacitive sensing unit 226 may include a portion having a capacitor array circuit 236 tuned for fingerprint detection, any such technology currently known or later developed may be modified for use herein, illustratively including the fingerprint sensor device disclosed in U.S. Pat. No. 9,990,533. In such an aspect, the handle 204 may include an indicia 238 for which the user places his/her finger for fingerprint detection. Alternatively, the entire capacitive sensing unit 226 may be configured for fingerprint detection. In such an aspect, a fingerprint may be detected wherever the handle 204 is gripped.

Figure 6:
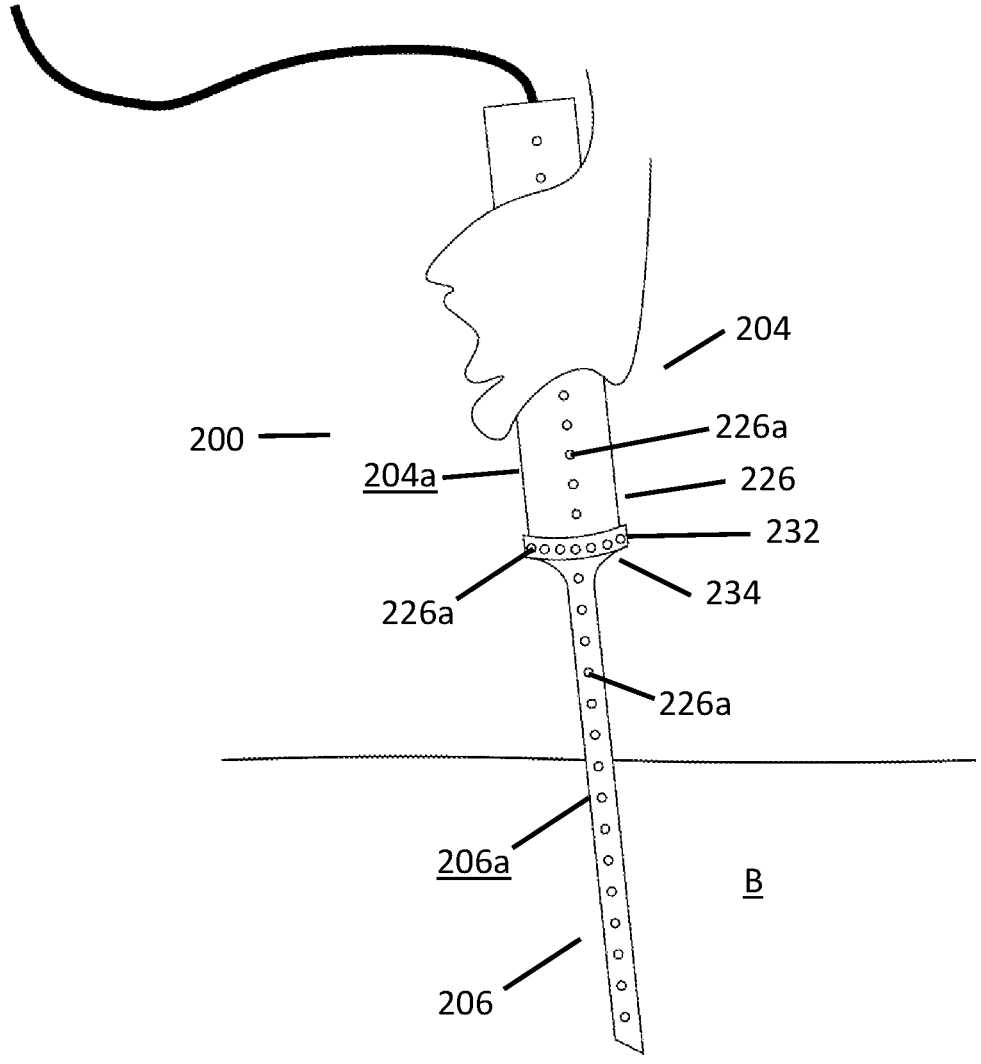
FIG. 6 is an illustrative depiction of a video endoscope is shown in FIG. 4 with the endoscope inserted into a patient and the handle is gripped.

With reference now to FIG. 6, another aspect of the video endoscope 200 is discussed, wherein a predetermined number of capacitive sensors 226a of the capacitive sensing unit 226 are disposed on the outer surface 206a of the endoscopic shaft 206 extends along a length of the endoscopic shaft 206. In such an aspect, the electronic controller 228 is further configured to process a signal detected by the capacitive sensors disposed on the outer surface 206a of the endoscopic shaft 206 when the endoscopic shaft 206 is inserted into a patient to determine a depth the endoscopic shaft 206 is inserted. As an example, assume that there are fifteen (15) capacitive sensors 226a disposed on the outer surface 206a of the endoscopic shaft 206 and the endoscopic shaft 206 is inserted into a patient ("B") a depth wherein eight (8) of the capacitive sensors 226a from the distal end of the endoscopic shaft 206 are inserted into the patient, the electronic controller 228 may processes the signal from the eight (8) capacitive sensors 226a so as to determine a depth that the endoscopic shaft 206 is inserted, e.g., 4.8 cm. Such information may be useful in medical procedures where a depth of an organ or other object of interest is known, or in diagnostic surgery to keep a detailed record of the location of an object of interest, such as a tumor or lesion within the body.

Figure 7:
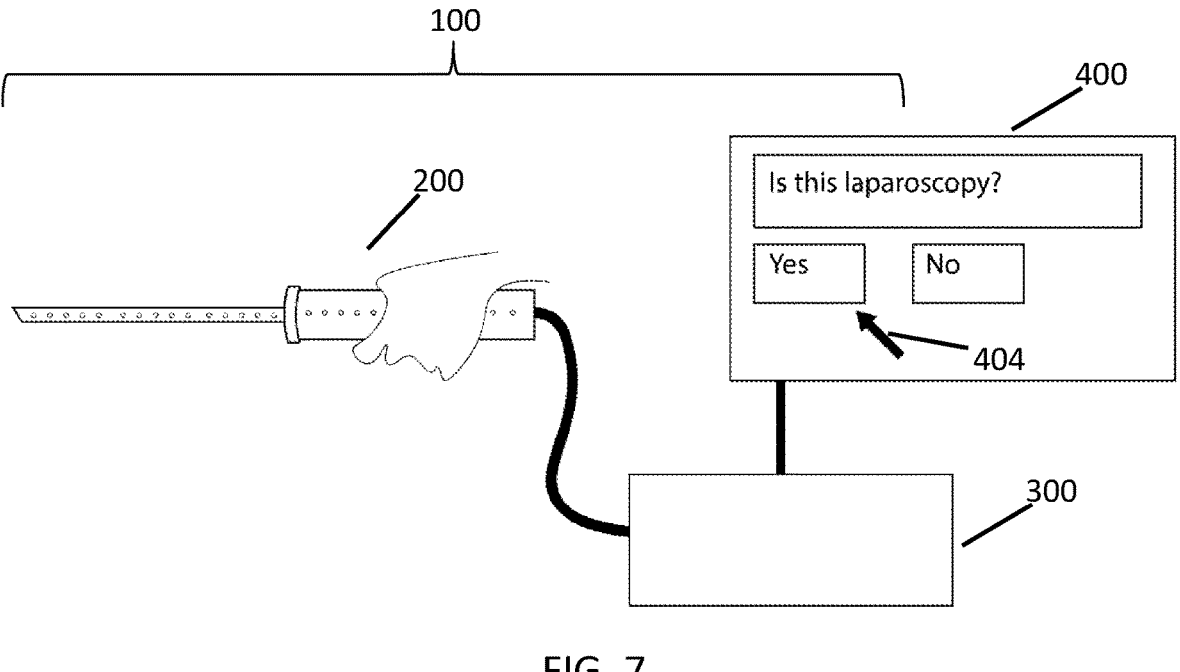
FIG. 7 is an illustrative depiction of an imaging system showing a determination and confirmation of a medical procedure.

With reference now to FIG. 7, a depiction of an imaging system 100 is provided wherein a medical procedure is determined. FIG. 7 shows the video endoscope 200 being gripped by the handle 204. The electronic controller 228 processes the detected grip and may determine a medical procedure. In the example, the electronic controller 228 determines that the medical procedure is a laparoscopy. The electronic controller 228 displays the determined medical procedure on the image display 402 and prompts the user to confirm the determined medical procedure. The user may confirm or reject the medical procedure by actuation of the user input 404. However, it should be appreciated that the electronic controller 228 may determine that a number of medical procedures may be associated with the detected grip. In such an aspect, the electronic controller 228 may provide a list of medical procedures associated with the detected grip wherein the user may select the appropriate medical procedure from the list. In such an aspect, a list of medical procedures may be stored in the second memory 230, with each of the medical procedure associated with a grip profile. The imaging system 100 may be further configured to adjust the camera operating parameters of the imaging system to camera operating parameters which are conducive to the selected or otherwise determined medical procedure, the camera operating parameters may be set by the electronic controller 228 or the system controller 308, such operating parameters may include: (1) an image sharpening function that selectively boosts the spatial frequencies associated with the surgical scene, e.g. liver texture, biliary duct structures etc; (2) a noise reduction function wherein the displayed frame rate is increased or decreased based upon the surgical procedure and (3) white balance function wherein the colors are set based upon the surgical procedure. As an example, should the user confirm that the medical procedure is a laparoscopy, certain camera settings could be activated. For example, in certain laparoscopy surgeries, the operation theater is a large body cavity. As a result a broad and uniform illumination distribution might be preferred, and therefore, as the result of identifying a laparoscopic surgery, directional LED illuminators on the distal end of the endoscopic shaft might all be activated. Once the camera operating parameters of the imaging system 100 are set, the user may manually adjust the camera operating parameters using the user inputs 404 so as to generate user parameters. In one aspect, the user parameters may be stored in association with a user profile in either the second memory 230 or the system memory 306. The benefit of such an aspect is described in further detail below.

Figure 8:
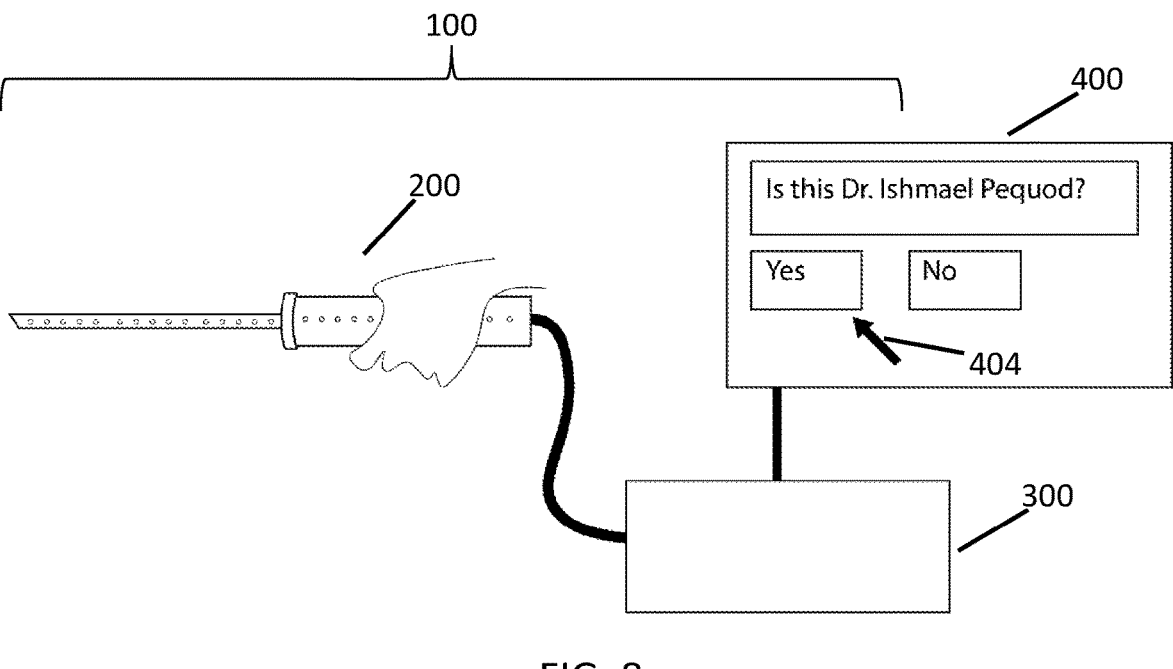
FIG. 8 is an illustrative depiction of an imaging system showing a determination and confirmation of an identification of a user.

With reference now to FIG. 8, a depiction of an imaging system 100 is provided wherein a user identity is determined. FIG. 8 shows the video endoscope 200 being gripped by the handle 204. The electronic controller 228 processes the detected grip and may determine a user identity. In this example, the user identity is determined by the detection of a fingerprint, but may be determined by other unique identifying biometric markers such as the grip profile. In the example, the electronic controller 228 processes a fingerprint to determine that the identity of the user is Dr. James Bailey. The electronic controller 228 displays the determined identity on the image display 402 and prompts the user to confirm the determined identity. The user may confirm or reject the identity by actuation of the user input 404. It should be appreciated that the identity of the user may also be done by processing the grip profile and associating the grip profile with a user. In such an instance, the user grips the handle 204, and the electronic controller stores the detected grip profile in the second memory 230 and prompts the user to enter his/her name, wherein the stored grip profile is associated with the user name and is stored in the second memory 230. Thus, the next time the user grips the handle 204, the electronic controller 228 processes the detected grip profile, retrieves the user name, displays the user name onto the image display 402, and prompts the user to confirm the determined identity.

In such an aspect, the user identity may be associated with a camera operating parameter of the imaging system 100. In addition, the user identity may be associated with a medical procedure wherein the medical procedure includes a camera operating parameter of the imaging system associated with the user. In such an aspect, the electronic controller 228 determines both the user identity and the medical procedure. The electronic controller 228 may prompt the user to confirm the determined user identity and the medical procedure, which may be done in no particular order. Upon confirmation of the user identity and the medical procedure, the electronic controller 228 and/or the system controller 308 configures the camera operating parameters of the imaging system 100 associated with the user and the medical procedure.

Figure 9:
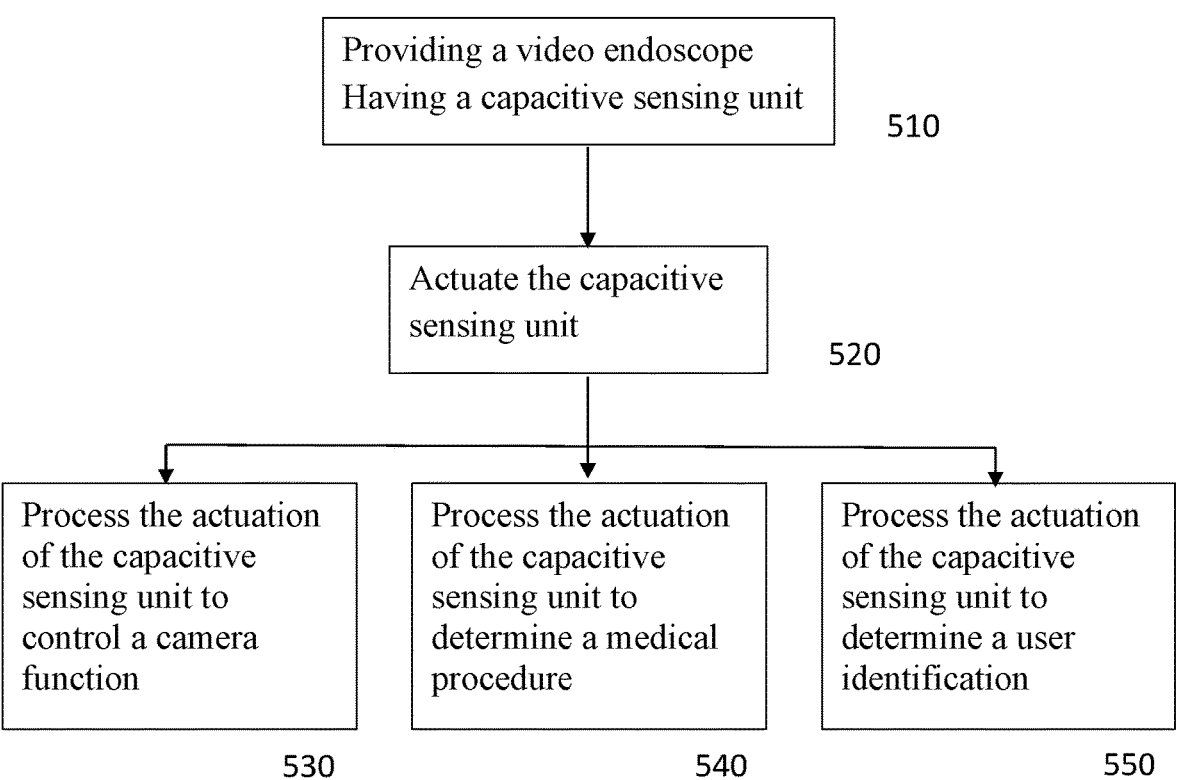
FIG. 9 is a flow chart showing the steps for a method of operating an imaging system.

With reference to FIG. 9, the steps of a method 500 of operating an imaging system 100 are also provided. At step 510, the method includes the step of providing a video endoscope 200. The video endoscope 200 includes an endoscopic shaft 206 having an image sensor 210 fixedly mounted within the endoscopic shaft 206 and a handle 204 attached to the endoscopic shaft 206. The video endoscope 200 further includes a capacitive sensing unit 226 disposed along an outer surface 204a of the handle 204, wherein the capacitive sensing unit 226 includes a plurality of capacitive sensors 226a arranged radially along the outer surface 204a of the handle 204.

At step 520, the method 500 includes the step of actuating the capacitive sensing unit 226. In one aspect, the actuation of the capacitive sensing unit 226 is done by sliding a finger along the capacitive sensing unit 226, and at step 530, the electronic controller 228 processes an actuation of the plurality of capacitive sensors 210a so as to control a camera function. In one aspect, the camera function is rotating the image in accordance with a direction of the slide. Accordingly, the orientation of the image may be adjusted by the user to a desired preference. In another aspect, the camera control function is turning off a light from the light source 208, wherein when no actuation of the capacitive sensing unit 226 is detected, e.g., the video scope 200 is not being held, the light source 208 is turned off, the display enters standby mode, etc.

The method 500 may further include the step of arranging the plurality of capacitive sensors 210a so as to form a ring 232. In some aspects a predetermined number of capacitive sensors 210a of the capacitive sensing unit 226 is further disposed on an outer surface 206a of the endoscopic shaft 206. In such an aspect, the method 500 may further include the step 540 of determining by the electronic controller 228 a medical procedure, wherein the electronic controller 228 processes a grip detected by the capacitive sensing unit 226 so as to determine the medical procedure. The method 500 may further include the step of displaying the medical procedure on an image display 402. In such an aspect, the method 500 may further include the step of confirming the medical procedure by actuating a user input 404 communicatively coupled to the camera control unit 300, as illustratively shown in FIG. 7.

In some implementations of the method 500, the method 500 may further include the step 550 of determining by the electronic controller 228, an identification of a user, wherein the electronic controller 228 processes a fingerprint detected by the capacitive sensing unit 226 to determine the identity of the user and may display the identification of the user on the image display 88. In such an implementation, the method 200 may further include the step of confirming the identification by actuating the user input 404 communicatively coupled to the camera control unit 300, wherein the user input 404 is further configured to enter a user identification. In yet another aspect of said implementation, the method 500 may further include the step of configuring a parameter of the video endoscope 200 to a user preference, the user preference associated with the identification determined by the electronic controller.

In yet another aspect of the method 500, some of the capacitive sensors 226a of the capacitive sensing unit 226 is disposed on an outer surface 206a of the endoscopic shaft 206 and extends along a length of the endoscopic shaft 206. In such an aspect, the method 200 further includes the step of calculating by the electronic controller 228, a depth of the endoscopic shaft 206 inserted into a patient, wherein the electronic controller 228 processes a signal detected by the capacitive sensors 226a of disposed on an outer surface 206a of the endoscopic shaft 206 when the endoscopic shaft 206 is inserted into a patient so as to calculate the depth in which the endoscopic shaft 206 is inserted.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A video endoscope comprising:

an endoscopic shaft including an image sensor fixedly mounted within the endoscopic shaft;

a handle fixedly attached to the endoscopic shaft, the handle including an electronic controller; and a capacitive sensing unit disposed along at least an outer surface of the handle, the capacitive sensing unit including a plurality of capacitive sensors arranged on at least the outer surface of the handle, wherein the electronic controller is operable to process an actuation of the plurality of capacitive sensors so as to control a camera control function;

wherein the electronic controller is configured to process a signal from the capacitive sensing unit to determine a grip profile;

wherein the electronic controller or a system controller in communication with the electronic controller includes a memory, and the memory includes a list of a plurality of medical procedures, each medical procedure having an associated grip profile; and wherein the electronic controller or system controller is configured to identify from said grip profile and said list, which medical procedure from a plurality of potential medical procedures is most likely being performed.

2. The video endoscope of claim 1, wherein the camera control function is a rotation of an image captured by the image sensor on a display.

3. The video endoscope of claim 2, wherein the plurality of capacitive sensors include an annular control ring, the plurality of capacitive sensors of the annular control ring being disposed radially about an axis of the handle, and being configured to affect the rotation of the captured image on the display.

4. The video endoscope of claim 3, wherein the annular control ring is disposed at a distal end of the handle, proximal to the shaft.

5. The video endoscope of claim 3, wherein the annular control ring is configured to affect the rotation of the captured image on the display such that a constant horizon is maintained.

6. The video endoscope of claim 1, wherein the camera control function is adjusting an intensity of illumination from a light source.

7. The video endoscope of claim 1, wherein a predetermined number of capacitive sensors of the capacitive sensing unit is further disposed on an outer surface of the endoscopic shaft.

8. The video endoscope of claim 7, wherein the predetermined number of capacitive sensors of the capacitive sensing unit disposed on the outer surface of the endoscopic shaft extends along a length of the endoscopic shaft.

9. The video endoscope of claim 8, wherein the electronic controller is further configured to process a signal detected by the predetermined number of capacitive sensors of the capacitive sensing unit disposed on the outer surface of the endoscopic shaft when the endoscopic shaft is inserted into a patient to determine a depth the endoscopic shaft is inserted, and wherein the camera control function adjusts a set of camera operating parameters, stored in the memory, and associated with the most likely medical procedure.

10. The video endoscope of claim 1, wherein the capacitive sensing unit is further configured to detect a biometric identifier and the electronic controller processes the biometric identifier so as to determine an identification of a user.

11. The video endoscope of claim 1, wherein the camera control function adjusts a set of camera operating parameters, stored in the memory, and associated with the medical procedure determined to be most likely being performed.

12. A method of operating an imaging system, the method comprising the steps of:

providing a video endoscope including:

an endoscopic shaft including an image sensor fixedly mounted within the endoscopic shaft;

a handle fixedly attached to the endoscopic shaft, the handle including a first electronic controller; and a capacitive sensing unit disposed along an outer surface of the handle, the capacitive sensing unit including a plurality of capacitive sensors arranged radially about a longitudinal axis of the handle on the outer surface of the handle and as an annular control ring;

sliding a finger along the annular control ring, wherein the electronic controller is further configured to process an actuation of the plurality of capacitive sensors so as to control a camera control function in accordance with a direction of the slide, processing a signal, by the electronic controller, from the capacitive sensing unit to determine a grip profile; and accessing a memory within the electronic controller or a system controller in communication with the electronic controller, the memory storing a list of a plurality of medical procedures, each of the plurality of medical procedures having an associated grip profile; and identifying from said grip profile and said list, which medical procedure from a plurality of potential medical procedures is most likely being performed, wherein a predetermined number of capacitive sensors of the capacitive sensing unit is further disposed on an outer surface of the endoscopic shaft, and wherein the camera control function includes rotating an image provided by the image sensor on a display in accordance with the direction of the slide.

13. The method of claim 12, wherein the predetermined number of capacitive sensors of the capacitive sensing unit disposed on the outer surface of the endoscopic shaft extends along a length of the endoscopic shaft; and further including the step of calculating by the electronic controller, a depth of the endoscopic shaft inserted into a patient, the electronic controller processing a signal detected by the predetermined number of capacitive sensors of the capacitive sensing unit disposed on the outer surface of the endoscopic shaft when the endoscopic shaft is inserted into the patient so as to calculate the depth in which the endoscopic shaft is inserted.

14. The method of claim 12, wherein the rotation of the image is configured to maintain a constant horizon when the annular control ring is touched and the endoscope is rotated about the longitudinal axis.

* * * * *